(12) United States Patent
Lewis, Jr.

(10) Patent No.: US 12,714,884 B2
(45) Date of Patent: Aug. 25, 2026

(54) ULTRASOUND COUPLING PATCH WITH GEL CAPTURE FEATURE

(71) Applicant: ZetrOZ Systems LLC, Trumbull, CT (US)

(72) Inventor: George K. Lewis, Jr., Trumbull, CT (US)

(73) Assignee: ZetrOZ Systems LLC, Trumbull, CT (US)

( * ) Notice: Subject to any disclaimer, the term of this patent is extended or adjusted under 35 U.S.C. 154(b) by 482 days.

(21) Appl. No.: 16/466,252

(22) PCT Filed: Dec. 4, 2017

(86) PCT No.: PCT/US2017/064564
§ 371 (c)(1),
(2) Date: Jun. 3, 2019

(87) PCT Pub. No.: WO2018/102828
PCT Pub. Date: Jun. 7, 2018

(65) Prior Publication Data

US 2020/0061393 A1 Feb. 27, 2020

Related U.S. Application Data

(60) Provisional application No. 62/429,788, filed on Dec. 3, 2016.

(51) Int. Cl.
*A61N 7/00* (2006.01)
*A61B 8/00* (2006.01)

(52) U.S. Cl.
CPC .............. *A61N 7/00* (2013.01); *A61B 8/4281* (2013.01); *A61N 2007/0004* (2013.01)

(58) Field of Classification Search
CPC ........................ A61N 7/00; A61N 2007/0004; A61B 8/4281; A61B 2017/2253; A61B 8/4411
See application file for complete search history.

(56) References Cited

U.S. PATENT DOCUMENTS

| | | | |
|---|---|---|---|
| 5,522,878 A | 6/1996 | Montecalvo et al. | |
| 5,626,554 A * | 5/1997 | Ryaby | A61N 7/00 601/2 |
| 5,782,767 A | 7/1998 | Pretlow, III | |
| 6,012,779 A * | 1/2000 | Morris | A61B 8/0875 310/336 |
| 2008/0033292 A1 | 2/2008 | Shafran | |
| 2008/0161693 A1* | 7/2008 | Prager | A61B 8/10 600/459 |
| 2008/0306388 A1 | 12/2008 | Tanis et al. | |
| 2010/0292576 A1 | 11/2010 | Krispi | |

(Continued)

OTHER PUBLICATIONS

International Searching Authority, International Search Report and Written Opinion issued in counterpart International Application No. PCT/US2017/064564, mailed Mar. 1, 2018.

(Continued)

*Primary Examiner* — Hien N Nguyen
(74) *Attorney, Agent, or Firm* — FisherBroyles, LLP; Andrew K. Gonsalves

(57) ABSTRACT

The present invention generally relates to, inter alia, an ultrasound coupling patch for use with ultrasound transducers, and more particularly to ultrasound coupling patches having a gel capture feature.

22 Claims, 9 Drawing Sheets

(56) References Cited

U.S. PATENT DOCUMENTS

| | | | | |
|---|---|---|---|---|
| 2013/0144193 | A1* | 6/2013 | Lewis, Jr. | A61B 8/4281 601/2 |
| 2015/0231415 | A1* | 8/2015 | Lewis, Jr. | A61B 8/4236 601/2 |
| 2016/0030001 | A1* | 2/2016 | Stein | A61B 8/06 600/431 |
| 2016/0136462 | A1 | 5/2016 | Lewis, Jr. et al. | |
| 2017/0128042 | A1* | 5/2017 | Desai | A61B 8/4281 |

OTHER PUBLICATIONS

European Patent Office, Extended European Search Report issued in counterpart European Patent Application No. EP 17875937.9, dated Jul. 13, 2020.

* cited by examiner 30c
10c
60c
60c
10c
60c
10c
60c
10c

ULTRASOUND COUPLING PATCH WITH GEL CAPTURE FEATURE

CROSS REFERENCE TO RELATED APPLICATIONS

This application is a U.S. National Phase filing under 35 U.S.C. § 371 of International Application No. PCT/US2017/064564, filed Dec. 4, 2017, and published as WO 2018/102828 A1 on Jun. 7, 2018, which claims priority benefit of U.S. Provisional Patent Application Ser. No. 62/429,788, filed Dec. 3, 2016, the disclosures of which are hereby incorporated by reference herein in their entirety.

FIELD OF THE INVENTION

The present invention generally relates to, inter alia, an ultrasound coupling patch for use with ultrasound transducers.

BACKGROUND OF THE INVENTION

Ultrasound technologies are used in a variety of imaging and therapeutic applications. For example, ultrasound is a widely recognized therapy used for the reduction of pain and inflammation and for acceleration of healing in patients with a wide range of injuries and other medical conditions. Until recently, the delivery of ultrasound therapy was limited to delivery by a medical professional in a professional healthcare setting. Smaller or more portable ultrasound devices (e.g., portable low intensity therapeutic ultrasound devices) can allow patients to self-administer ultrasound therapy outside the professional healthcare setting.

In ultrasound therapy applications, ultrasonic waves are produced by a transducer of a portable low intensity therapeutic ultrasonic device. The transducer is applied to the skin in the area of treatment. In order for the ultrasonic waves to leave the transducer and penetrate the skin, an acoustic gel has commonly been used as a coupling agent. The acoustic gel, which is applied between the target area, specifically the skin, and the transducer, tends to be applied in unmeasured amounts. Due to the unknown application amounts it is difficult to estimate the actual amount of acoustic energy that is delivered to the target area, and the efficiency of energy coupling from the transducer to the skin. Additionally, the current methods of applying the acoustic gel tend to be messy and inappropriate for patient self-administered low intensity therapeutic ultrasound treatment.

With the advent of patient self-administered low intensity therapeutic ultrasound, a method is required that assures the proper amount of an ultrasonic coupling agent is available between the transducer of the low intensity therapeutic ultrasound device and the target area and that such method of application of the coupling agent is sufficiently simple for a patient to use during the treatment period.

Further, therapeutic ultrasound devices are not able to be used for long periods, due to the non-portable size of the devices or the need for external power sources.

Previous attempts to provide bandages and other coupling devices for use with therapeutic ultrasound technologies have been reported. See, e.g., U.S. Pat. No. 4,787,888, U.S. Pat. No. 7,211,060, and U.S. Patent Application Publication No. US-2008/0200810. However, the ultrasound bandages or coupling devices provided in the art to date are insufficient for use with portable therapeutic ultrasound systems that are able to deliver ultrasound energy deep within tissue and that can be used for long periods of time.

There is also a need for ultrasound coupling devices that can be used with all types of ultrasound transducers, not just therapeutic ultrasound transducers, and that can enhance the efficiency of ultrasound transmission to a subject.

The present invention is directed to overcoming these and other deficiencies in the art.

SUMMARY OF THE INVENTION

The present invention generally relates to, inter alia, an ultrasound coupling patch for use with ultrasound transducers, and more particularly to ultrasound coupling patches having a gel capture feature.

The present invention allows for a new coupling agent capture feature to be added to the ultrasound coupling patch, thereby controlling the movement of coupling agent during the insertion of the device into the patch for preferable coupling.

In one aspect, the present invention provides an ultrasound coupling device that includes: (i) a gel component comprising a gel material effective to conduct acoustic energy; and (ii) a coupling compartment effective for holding the gel component in place. The coupling compartment includes: a wall-like structure having a sidewall, a top portion, and a bottom portion; a top seal removably integrated to the top portion of the wall-like structure; and a bottom seal removably integrated to the bottom portion of the wall-like structure. The bottom seal is preformed to hold a desired volume of the gel material between an ultrasound transducer and the bottom seal when said ultrasound transducer is attached at the top portion of the wall-like structure. The gel component is contained at least within a portion of a sidewall of the wall-like structure of the coupling compartment and at least a portion outside of the wall-like structure.

In another aspect, the present invention provides an ultrasound coupling device that includes: (i) a gel component comprising a gel material effective to conduct acoustic energy; and (ii) a coupling compartment effective for holding the gel component in place. The coupling compartment includes: a wall-like structure having a sidewall, a top portion, and a bottom portion; a top seal removably integrated to the top portion of the wall-like structure; and a bottom seal removably integrated to the bottom portion of the wall-like structure. The bottom seal is expandable to hold a desired volume of the gel material between an ultrasound transducer and the bottom seal when said ultrasound transducer is attached at the top portion of the wall-like structure. The gel component is contained at least within a portion of a sidewall of the wall-like structure of the coupling compartment and at least a portion outside of the wall-like structure.

In yet another aspect, the present invention provides an ultrasound coupling device that includes: (i) a gel component comprising a gel material effective to conduct acoustic energy; and (ii) a coupling compartment effective for holding the gel component in place. The coupling compartment includes: a wall-like structure having a sidewall, a top portion, and a bottom portion; a top seal removably integrated to the top portion of the wall-like structure; and a bottom seal removably integrated to the bottom portion of the wall-like structure. The top and bottom seals are formed to hold a known volume of gel in a defined location within the coupling compartment.

In one aspect, the present invention provides an ultrasound coupling system that includes: (i) any of the ultrasound coupling devices disclosed herein; and (ii) an ultrasound transducer configured for operable attachment to the ultrasound coupling device.

In another aspect, the present invention provides a method for performing physiotherapy on a subject. This method involves: (i) providing any of the ultrasound coupling systems disclosed herein; and (ii) using the system to apply therapeutic ultrasound energy to a subject, where the therapeutic ultrasound energy is generated by the transducer and emitted through the gel component of the coupling device.

In another aspect, the present invention provides a method for applying ultrasound energy to a subject. This method involves: (i) providing any of the ultrasound coupling systems disclosed herein; and (ii) using the system to apply ultrasound energy to a surface of a subject, where the ultrasound energy is generated by the transducer and emitted through the gel component of the coupling device.

In certain embodiments, the ultrasound coupling device is referred to herein as an ultrasound coupling patch that secures an ultrasound transducer to a patient for extended treatment periods and also acts to couple the ultrasound produced from the device into the patient. A portion of the ultrasound coupling patch maintains a coupling agent (e.g., ultrasound gel, hydrogel or equivalent) between the ultrasound emitting surface of the ultrasound transducer) and the part of the body to which ultrasound is being applied. Another portion of the patch provides adhesive properties to secure the device onto a location of the body. Current versions of the ultrasound coupling patch work well for this purpose (see US-2013/0144193-A1 and EP 2519322-A2), however there are some challenges in using the ultrasound coupling patch devices currently known in the art.

For example, with existing ultrasound coupling patches, when the ultrasound device is secured into the patch, excess coupling agent in the patch does not move in a controlled direction. In some cases, the ultrasound gel can move out the sides/top of the device away from the device/body interface in which it is intended. This creates an unwanted mess and loss of coupling gel between the ultrasound transducer and patient. Further, because the seal on the bottom of the patch is flat, it does not allow for a measured amount of gel to form outside of the patch between the device and body, to allow for ample coupling agent to fill various forms of the human body. The ultrasound coupling device is effective to remedy these and other deficiencies in the art.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

DETAILED DESCRIPTION OF THE INVENTION

Figure 1:
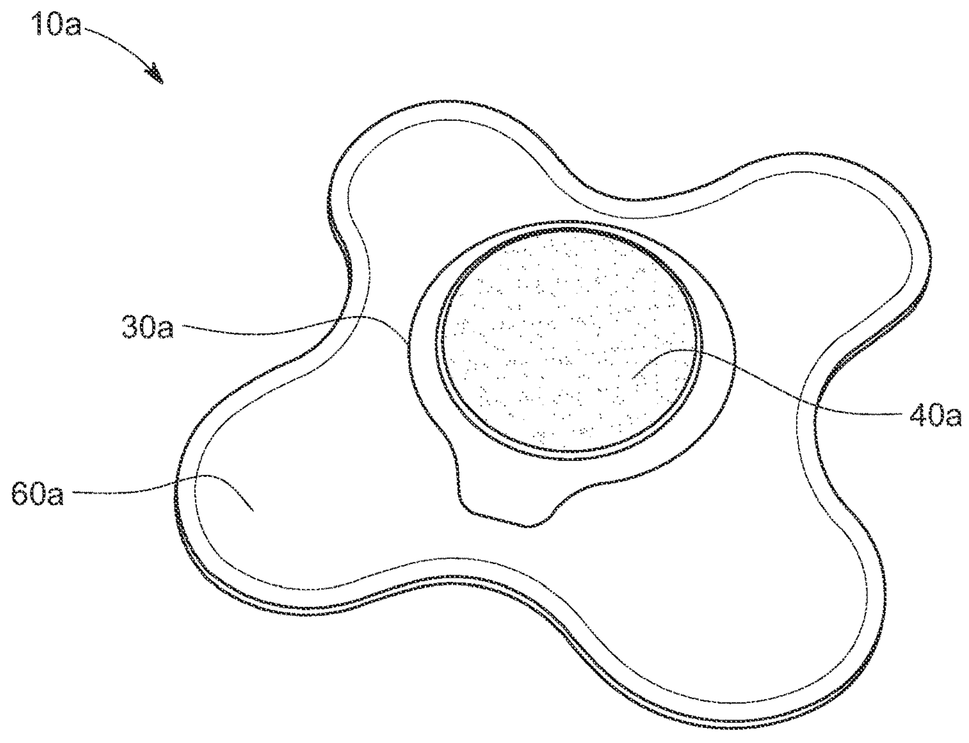
FIG. 1 is a top view of one embodiment of an ultrasound coupling device of the present invention.

The present invention relates to an ultrasound coupling device, as further described herein. The present invention also relates to various ultrasound kits and ultrasound transducer systems configured to include the ultrasound coupling device of the present invention. Further, the present invention relates to various methods of using and making the ultrasound coupling device of the present invention.

The ultrasound coupling device of the present invention has various attributes, as described more fully herein. Without meaning to limit the present invention to a particular embodiment, provided below are various attributes of the present invention.

The present invention provides a simple and disposable means to connect an ultrasound transducer or low profile ultrasound transducer or ultrasound therapy device to a specific region of a patient without having the need to manually hold the ultrasound transducer in place on the body. The invention makes the application of ultrasound therapy or ultrasound in combination with a topical pharmaceutical to be a simple and self-delivered process.

In one aspect, the present invention provides an affordable, highly adaptable and ergonomic means to secure ultrasound coupling gel to the face of an ultrasound transducer, and couple it to a patient or other object.

The ultrasound coupling device of the present invention may be used for ultrasound therapy, imaging, monitoring, industrial measurements and testing, anywhere ultrasound would be applied and requires attachment to some type of object or subject.

As referred to herein, the ultrasound coupling device may also be referred to as a specific embodiment for use as a hydrogel low-intensity ultrasound (LIUS) coupling patch device or variants thereof. However, the ultrasound coupling device of the present invention is useful for all types of ultrasound applications (e.g., imaging and therapeutic applications), and the gel is not limited to a hydrogel, but can include any type of gel or gel-like substance that can be used with ultrasound. Further, the ultrasound coupling device of the present invention can be used with various types of ultrasound transducers. In one embodiment, a suitable ultrasound transducer or ultrasound system for use with the ultrasound coupling device of the present invention can include, without limitation, a portable, low-profile type of ultrasound transducer.

Examples of portable ultrasound systems that can be used with the ultrasound coupling device of the present invention are provided in WO2011/082407, the entire disclosure of which is incorporated by reference herein.

Examples of low-profile ultrasound transducers that can be used with the ultrasound coupling device of the present invention are provided in WO2011/082408, the entire disclosure of which is incorporated by reference herein.

As provided herein, the gel component can be a hydrogel or any type of gel or gel-like substance that can be used with ultrasound. Therefore, in describing the various aspects and embodiments of the present invention, the term "hydrogel" can be used to refer to a hydrogel or any gel or gel-like substance that can be used with ultrasound.

In various embodiments, the gel component can be a hydrogel that is made of polymer materials that can absorb large amounts of water without dissolving due to physical or chemical cross-linkage of the hydrophilic polymer chains. Hydrogels which have low density cross-linking are more suitable conducting acoustic energy but low density cross-linking causes the hydrogel to be less ridged. The present invention is effective for using such hydrogels (as well as any other gel or gel-like material) for conducting acoustic energy from a low intensity ultrasound device to a subject.

In one aspect, the present invention provides a hydrogel LIUS coupling patch device that is designed to serve as an efficient acoustic conductive vehicle for the transmission of low intensity ultrasound between the portable low intensity therapeutic ultrasound device and the skin.

In one aspect, the present invention relates to the manufacture, composition, and use of biocompatible hydrogel acoustic coupling patches for transfer of low intensity therapeutic ultrasound to achieve pain relief, reduction of inflammation and healing.

A suitable gel component can include, for example, a hydrogel material effective to conduct acoustic energy. In one embodiment, the hydrogel material, gel material, or gel-like material is effective to conduct acoustic energy across the entire therapy range, e.g., from about 10 to about 100,000,000 mW/cm2. The acoustic energy can be in the form of low-intensity ultrasound waves. As stated above, the hydrogel material, gel material, or gel-like material is effective to conduct low-intensity ultrasound waves ranging from about 10 to about 100,000,000 mW/cm2. The present invention also contemplates that suitable hydrogel materials, gel materials, or gel-like materials are effective to conduct low-intensity ultrasound waves at any value within the range of 10 to about 100,000,000 mW/cm2. While not meaning to limit the present invention, examples of various suitable ranges of low-intensity ultrasound waves can include, without limitation, a range selected from the group consisting of between about 10 mW/cm2 to about 50,000,000 mW/cm2, between about 10 mW/cm2 to about 1,000,000 mW/cm2, between about 10 mW/cm2 to about 500,000 mW/cm2, between about 10 mW/cm2 to about 250,000 mW/cm2, between about 10 mW/cm2 to about 100,000 mW/cm2, between about 10 mW/cm2 to about 50,000 mW/cm2, between about 10 mW/cm2 to about 40,000 mW/cm2, between about 10 mW/cm2 to about 30,000 mW/cm2, between about 10 mW/cm2 to about 20,000 mW/cm2, between about 10 mW/cm2 to about 10,000 mW/cm2, between about 10 mW/cm2 to about 6,000 mW/cm2, between about 10 mW/cm2 to about 5,750 mW/cm2, between about 10 mW/cm2 to about 5,500 mW/cm2, between about 10 mW/cm2 to about 5,250 mW/cm2, between about 10 mW/cm2 to about 5,000 mW/cm2, between about 10 mW/cm2 to about 4,750 mW/cm2, between about 10 mW/cm2 to about 4,500 mW/cm2, between about 10 mW/cm2 to about 4,250 mW/cm2, between about 10 mW/cm2 to about 4,000 mW/cm2, between about 10 mW/cm2 to about 3,750 mW/cm2, between about 10 mW/cm2 to about 3,500 mW/cm2, between about 10 mW/cm2 to about 3,250 mW/cm2, between about 10 mW/cm2 to about 3,000 mW/cm2, between about 10 mW/cm2 to about 2,750 mW/cm2, between about 10 mW/cm2 to about 2,500 mW/cm2, between about 10 mW/cm2 to about 2,250 mW/cm2, between about 10 mW/cm2 to about 2,000 mW/cm2, between about 10 mW/cm2 to about 1,750 mW/cm2, between about 10 mW/cm2 to about 1,500 mW/cm2, between about 10 mW/cm2 to about 1,250 mW/cm2, between about 10 mW/cm2 to about 1,000 mW/cm2, between about 10 mW/cm2 to about 750 mW/cm2, between about 10 mW/cm2 to about 500 mW/cm2, between about 10 mW/cm2 to about 250 mW/cm2, between about 10 mW/cm2 to about 200 mW/cm2, between about 10 mW/cm2 to about 150 mW/cm2, and between about 10 mW/cm2 to about 100 mW/cm2.

The present invention generally relates to, inter alia, an ultrasound coupling patch for use with ultrasound transducers, and more particularly to ultrasound coupling patches having a gel capture feature. The present invention allows for a new coupling agent capture feature to be added to the ultrasound coupling patch, thereby controlling the movement of coupling agent during the insertion of the device into the patch for preferable coupling. As used herein, the term "ultrasound coupling device" can be used to refer to the ultrasound coupling patch of the present invention.

Provided below are various embodiments of an ultrasound coupling device of the present invention. The ultrasound coupling device of the present invention can involve the use of various elements and components described in WO2015/130841, US2013/0144193, WO2011/082407, and WO2011/082408, the entire disclosure of which is incorporated by reference herein.

Pre-Formed Seal to Hold a Known Volume of Coupling Agent in Front of an Ultrasound Device In a first aspect, the present invention provides an ultrasound coupling device that includes: (i) a gel component comprising a gel material effective to conduct acoustic energy; and (ii) a coupling compartment effective for holding the gel component in place. The coupling compartment includes: a wall-like structure having a sidewall, a top portion, and a bottom portion; a top seal removably integrated to the top portion of the wall-like structure; and a bottom seal removably integrated to the bottom portion of the wall-like structure. The bottom seal is preformed to hold a desired volume of the gel material between an ultrasound transducer and the bottom seal when said ultrasound transducer is attached at the top portion of the wall-like structure. The gel component is contained at least within a portion of a sidewall of the wall-like structure of the coupling compartment and at least a portion outside of the wall-like structure.

In one embodiment of this coupling device of the present invention, the top and bottom seals are made from aluminum foil.

In another embodiment, the preformed bottom seal is integrated with an adhesive retainer liner of the coupling device.

In another embodiment, the gel material is selected from the group consisting of a gel, a gel-like composition, a hydrogel, a low density cross-linked polymer hydrogel, and the like.

In another embodiment, the gel material is provided so as to have a thickness of between 0.25 mm and about 10 mm (including any measurement contained between 0.25 mm and 10 mm), and a shape of the performed seal to accommodate the ultrasound transducer.

In another embodiment, this ultrasound coupling device further includes an adhesive fabric for interfacing the coupling device with a subject, where the adhesive fabric includes a vacant area in which the coupling compartment is situated for operation.

In another aspect, the present invention provides an ultrasound coupling system that includes: (i) the ultrasound coupling device disclosed herein above; and (ii) an ultrasound transducer configured for operable attachment to the ultrasound coupling device.

In another aspect, the present invention provides a method for performing physiotherapy on a subject. This method involves: (i) providing the ultrasound coupling system disclosed herein above; and (ii) using the system to apply therapeutic ultrasound energy to a subject, where the therapeutic ultrasound energy is generated by the transducer and emitted through the gel component of the coupling device.

In another aspect, the present invention provides a method for applying ultrasound energy to a subject. This method involves: (i) providing the ultrasound coupling system disclosed herein above; and (ii) using the system to apply ultrasound energy to a surface of a subject, where the ultrasound energy is generated by the transducer and emitted through the gel component of the coupling device. In one embodiment, applying the ultrasound energy to the surface of the subject is effective to alleviate pain in tissue of the subject in and around the surface.

FIGS. 1-8 illustrate various aspects of the above-described embodiment of the ultrasound coupling device of the present invention. With respect to FIGS. 1-8, the reference numbers of this embodiment of the ultrasound coupling device are identified in the paragraph below, as follows: As shown in FIGS. 1-8, ultrasound coupling device 10*a* includes: (i) a gel component 20*a* comprising a gel material effective to conduct acoustic energy; and (ii) a coupling compartment 30*a* effective for holding gel component 20*a* in place. Coupling compartment 20*a* includes: wall-like structure 32*a* having sidewall 33*a*, top portion 34*a*, and bottom portion 35*a*; top seal 40*a* removably integrated to top portion 34*a* of wall-like structure 32*a*; and bottom seal 42*a* removably integrated to bottom portion 35*a* of wall-like structure 32*a*. Bottom seal 42*a* is preformed to hold a desired volume of the gel material between ultrasound transducer 50*a* and bottom seal 42*a* when ultrasound transducer 50*a* is attached at top portion 34*a* of wall-like structure 32*a*. Gel component 20*a* is contained at least within a portion of sidewall 33*a* of wall-like structure 32*a* of coupling compartment 30*a* and at least a portion outside of wall-like structure 32*a*. Ultrasound coupling device 10*a* can further include adhesive fabric 60*a* for interfacing coupling device 10*a* with a subject, where adhesive fabric 60*a* includes a vacant area in which coupling compartment 30*a* is situated for operation.

FIG. 1 illustrates the top of the ultrasound coupling device with a top seal and gel-containment structure.

Figure 2:
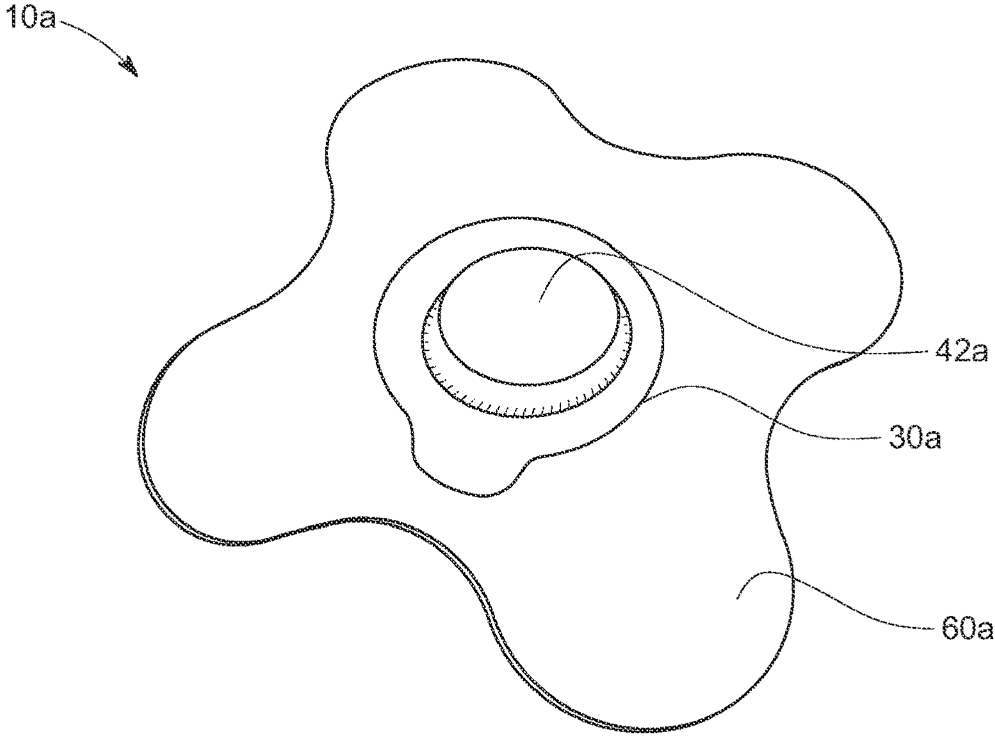
FIG. 2 is a bottom view of one embodiment of an ultrasound coupling device of the present invention.

FIG. 2 illustrates the bottom of the ultrasound coupling device with a pre-formed seal on the bottom. Inside of the device is a sealed volume of ultrasound gel.

Figure 3:
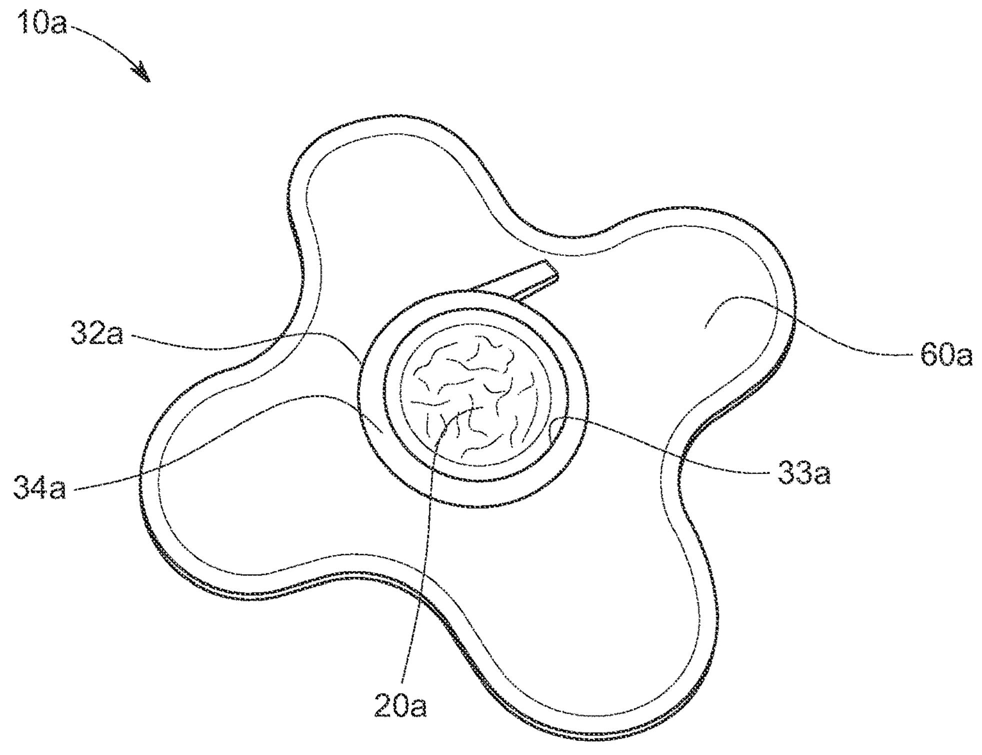
FIG. 3 is a top view of one embodiment of an ultrasound coupling device of the present invention.

FIG. 3 illustrates the top of the ultrasound coupling device with a top seal removed with a known quantity of coupling gel sealed within patch (shown in light blue).

Figure 4:
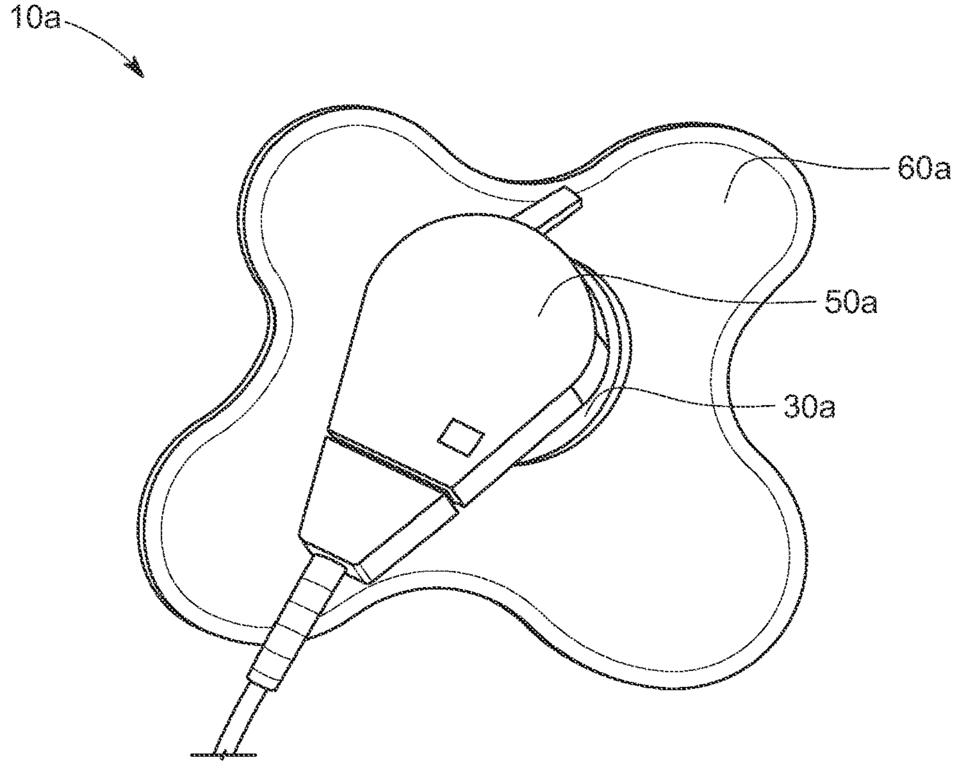
FIG. 4 is a top view of one embodiment of an ultrasound coupling device of the present invention, showing an ultrasound transducer coupled with the ultrasound coupling device of the present invention.

As shown in FIG. 4, when the ultrasound transducer is clipped into the ultrasound coupling patch, the ultrasound gel within the device moves in a forward direction with no gel escaping from the device and fully coating the ultrasound transducer surface.

Figure 5:
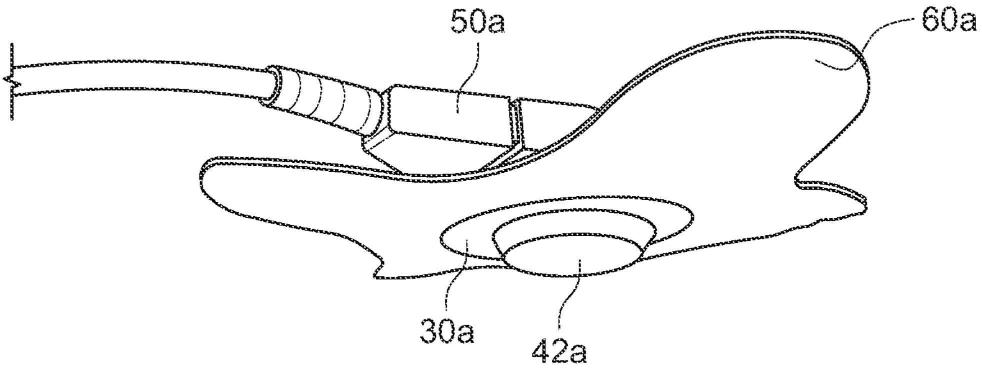
FIG. 5 is a side/bottom view of one embodiment of an ultrasound coupling device of the present invention, showing an ultrasound transducer coupled with the ultrasound coupling device of the present invention.

FIG. 5 illustrates the side/bottom view of the ultrasound transducer clipped into ultrasound coupling device. As shown, the gel is captured between the ultrasound transducer and bottom pre-formed seal.

Figure 6:
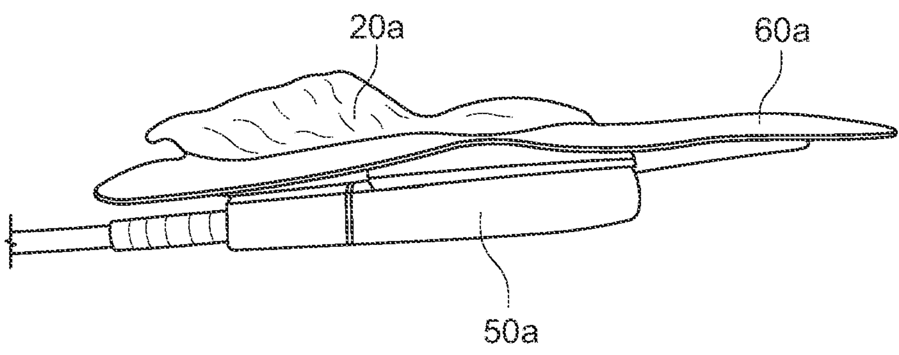
FIG. 6 is a side view of one embodiment of an ultrasound coupling device of the present invention, showing the bottom of the ultrasound coupling device facing up with its pre-formed bottom seal removed.

As shown in FIG. 6, when the bottom pre-formed seal is removed, the ultrasound coupling gel is contained within and extends beyond the bottom surface of the ultrasound coupling patch and the gel-containment structure. This gel fills any voids of cavities where the ultrasound coupling device is applied to the body.

Figure 7:
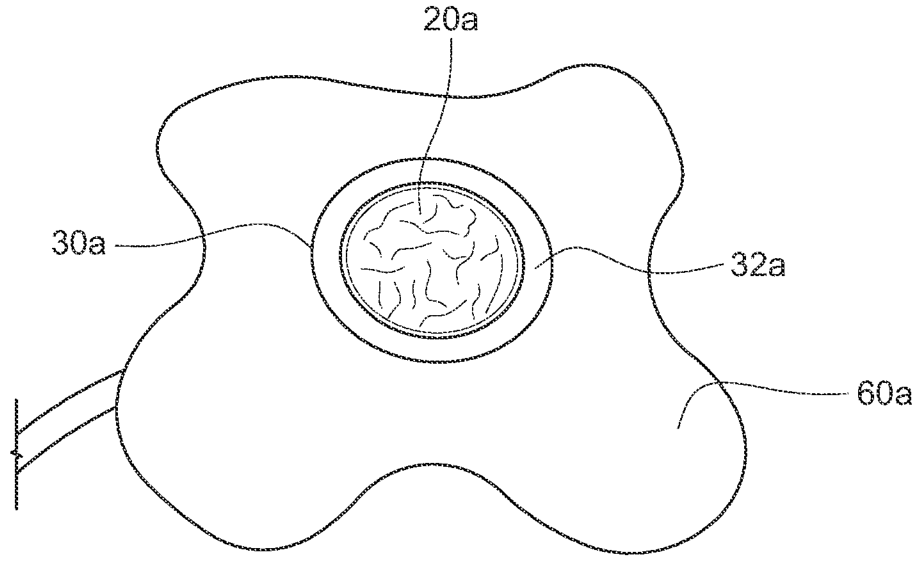
FIG. 7 is a bottom view of one embodiment of an ultrasound coupling device of the present invention, illustrating an adhesive retainer liner of the patch of the present invention.

As shown in FIG. 7, the adhesive retainer liner of the patch is removed and ultrasound gel is shown in blue between the ultrasound transducer and the patch surface.

Figure 8:
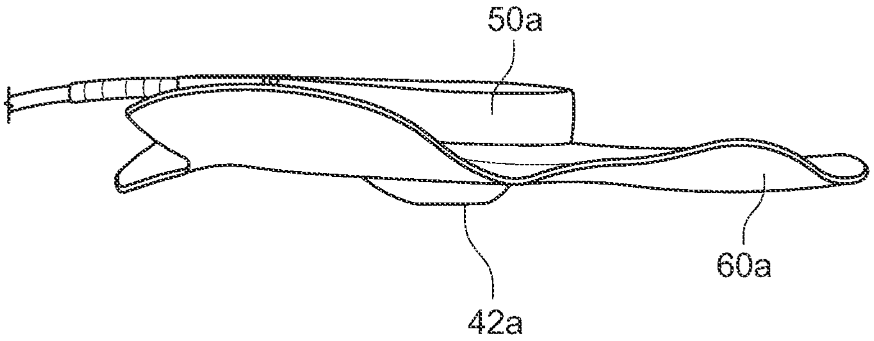
FIG. 8 is a side view of one embodiment of an ultrasound coupling device of the present invention, showing an ultrasound transducer coupled with the ultrasound coupling device of the present invention.

FIG. 8 illustrates a side view of the ultrasound coupling device and a known quantity of gel captured in front of ultrasound transducer.

Expandable Seal to Control and Position a Known Volume of Coupling Agent in Front of the Ultrasound Device In a second aspect, and similar to the above described embodiment of the ultrasound coupling device, the present invention relates to a configuration in which the seal is made of foil (folded/crinkled) or a flexible material in a flat form factor which is able to expand outward when the transducer is inserted into the chamber displacing the ultrasound gel in the forward direction, as discussed below and illustrated in FIGS. 9-13.

In this aspect, there is provided an ultrasound coupling device that includes: (i) a gel component comprising a gel material effective to conduct acoustic energy; and (ii) a coupling compartment effective for holding the gel component in place. The coupling compartment includes: a wall-like structure having a sidewall, a top portion, and a bottom portion; a top seal removably integrated to the top portion of the wall-like structure; and a bottom seal removably integrated to the bottom portion of the wall-like structure. The bottom seal is expandable to hold a desired volume of the gel material between an ultrasound transducer and the bottom seal when said ultrasound transducer is attached at the top portion of the wall-like structure. The gel component is contained at least within a portion of a sidewall of the wall-like structure of the coupling compartment and at least a portion outside of the wall-like structure.

In one embodiment of this coupling device of the present invention, the expandable bottom seal is made from an elastic material which expands outward upon insertion of the ultrasound transducer.

In another embodiment, the expandable bottom seal is made from an aluminum foil seal which expands outward upon insertion of the ultrasound transducer.

In another embodiment, the gel material is selected from the group consisting of a gel, a gel-like composition, a hydrogel, a low density cross-linked polymer hydrogel, and the like.

In another embodiment, the gel material is provided so as to have a thickness of between 0.25 mm and about 10 mm (including any measurement contained between 0.25 mm and 10 mm), and a shape of the performed seal to accommodate the ultrasound transducer.

In another embodiment, this ultrasound coupling device further includes an adhesive fabric for interfacing the coupling device with a subject, where the adhesive fabric includes a vacant area in which the coupling compartment is situated for operation.

In another aspect, the present invention provides an ultrasound coupling system that includes: (i) the ultrasound coupling device disclosed herein above; and (ii) an ultrasound transducer configured for operable attachment to the ultrasound coupling device.

In another aspect, the present invention provides a method for performing physiotherapy on a subject. This method involves: (i) providing the ultrasound coupling system disclosed herein above; and (ii) using the system to apply therapeutic ultrasound energy to a subject, where the therapeutic ultrasound energy is generated by the transducer and emitted through the gel component of the coupling device.

In another aspect, the present invention provides a method for applying ultrasound energy to a subject. This method involves: (i) providing the ultrasound coupling system disclosed herein above; and (ii) using the system to apply ultrasound energy to a surface of a subject, where the ultrasound energy is generated by the transducer and emitted through the gel component of the coupling device. In one embodiment, applying the ultrasound energy to the surface of the subject is effective to alleviate pain in tissue of the subject in and around the surface.

FIGS. 9-13 illustrate various aspects of the above-described embodiment of the ultrasound coupling device of the present invention. With respect to FIGS. 9-13, the reference numbers of this embodiment of the ultrasound coupling device are identified in the paragraph below, as follows: As shown in FIGS. 9-13, ultrasound coupling device 10*b* includes: (i) gel component 20*b* comprising a gel material effective to conduct acoustic energy; and (ii) coupling compartment 30*b* effective for holding gel component 20*b* in place. Coupling compartment 30*b* includes: wall-like structure 32*b* having sidewall 33*b*, top portion 34*b*, and bottom portion 35*b*; top seal 40*b* removably integrated to top portion 34*b* of the wall-like structure 32*b*; and bottom seal 42*b* removably integrated to bottom portion 35*b* of wall-like structure 32*b*. Bottom seal 42*b* is expandable to hold a desired volume of the gel material between ultrasound transducer 50*b* and bottom seal 42*b* when ultrasound transducer 50*b* is attached at top portion 34*b* of wall-like structure 32*b*. Gel component 20*b* is contained at least within a portion of sidewall 33*b* of wall-like structure 32*b* of coupling compartment 30*b* and at least a portion outside of wall-like structure 32*b*. Ultrasound coupling device 10*b* can further include adhesive fabric 60*b* for interfacing coupling device 10*b* with a subject, where adhesive fabric 60*b* includes a vacant area in which coupling compartment 30*b* is situated for operation.

Figure 9:
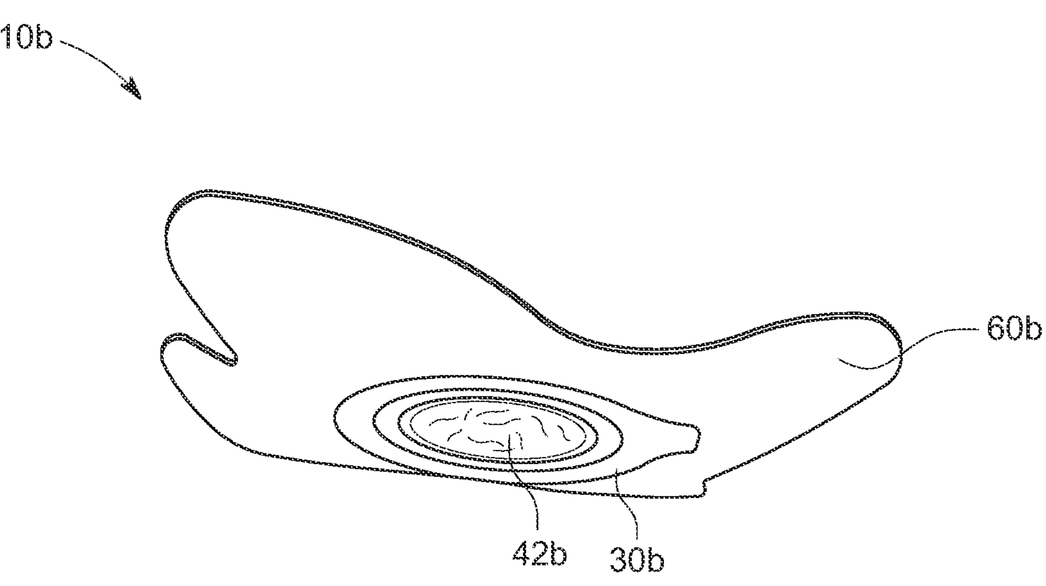
FIG. 9 is a bottom view of one embodiment of an ultrasound coupling device of the present invention, illustrating a flat foil bottom seal on the bottom of the ultrasound coupling device patch which has crinkles in the bottom seal to allow for expansion when pressure is applied to the bottom seal from an ultrasound transducer.

FIG. 9 illustrates the ultrasound coupling device with a flat foil seal on the bottom of the patch which has crinkles in the seal to allow for expansion when pressure is applied to the device. The profile of the seal is flat and does not protrude from the bottom of the ultrasound coupling device.

Figure 10:
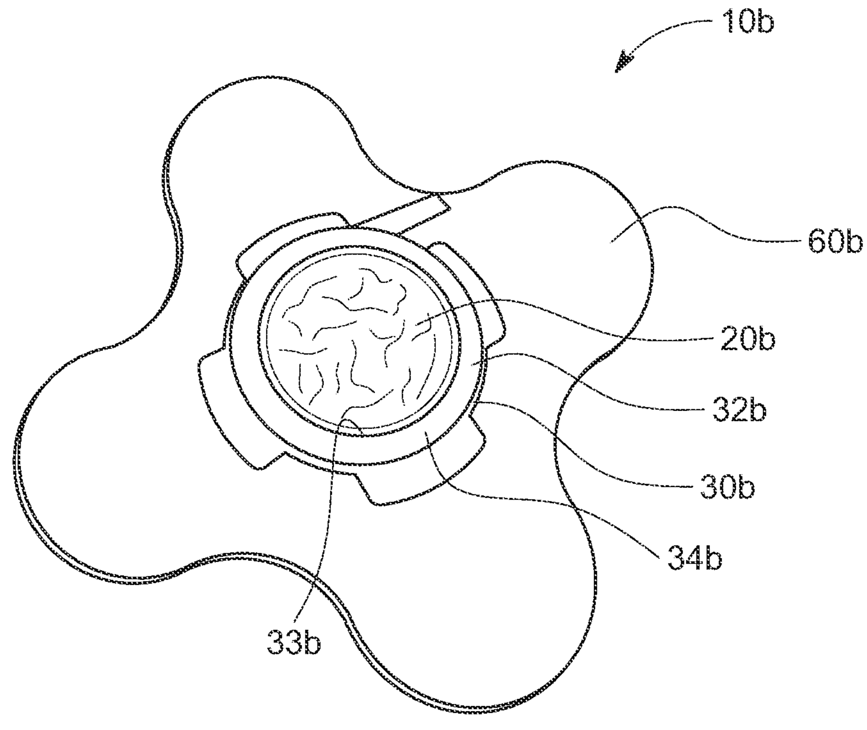
FIG. 10 is a top view of one embodiment of an ultrasound coupling device of the present invention.

FIG. 10 illustrates the top side of the ultrasound coupling device, illustrating the crinkle in the bottom foil seal, along with the ultrasound coupling gel in light blue.

Figure 11:
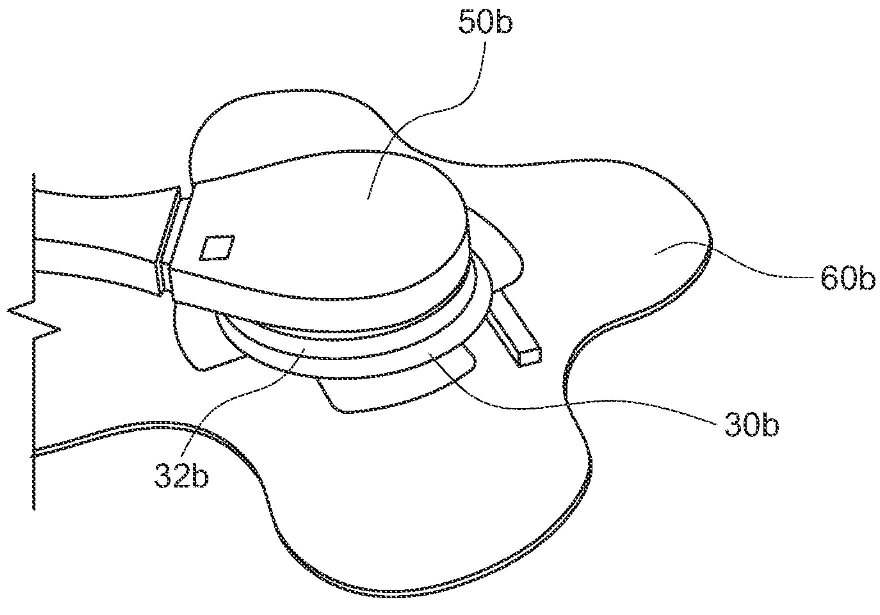
FIG. 11 is a top view of one embodiment of an ultrasound coupling device of the present invention, showing an ultrasound transducer coupled with the ultrasound coupling device of the present invention.

FIG. 11 illustrates the ultrasound transducer inserted into the ultrasound coupling device causing the gel to displace in the forward direction pushing out the expandable foil seal.

Figure 12:
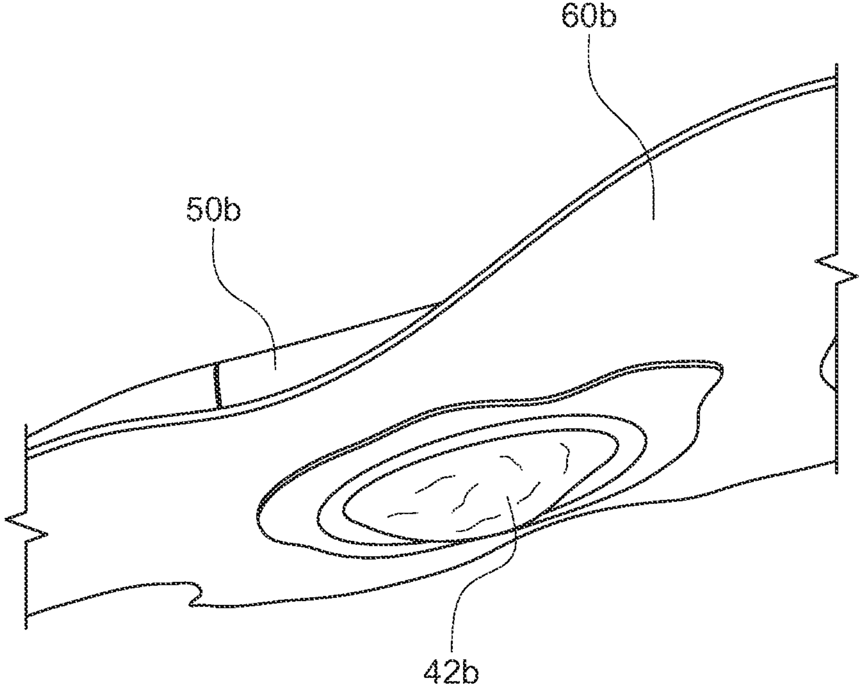
FIG. 12 is a side/bottom view of one embodiment of an ultrasound coupling device of the present invention.

FIG. 12 illustrates the underside view of the device, showing how the foil expands outward with gel inside protruding beyond the base of the ultrasound coupling device.

Figure 13:
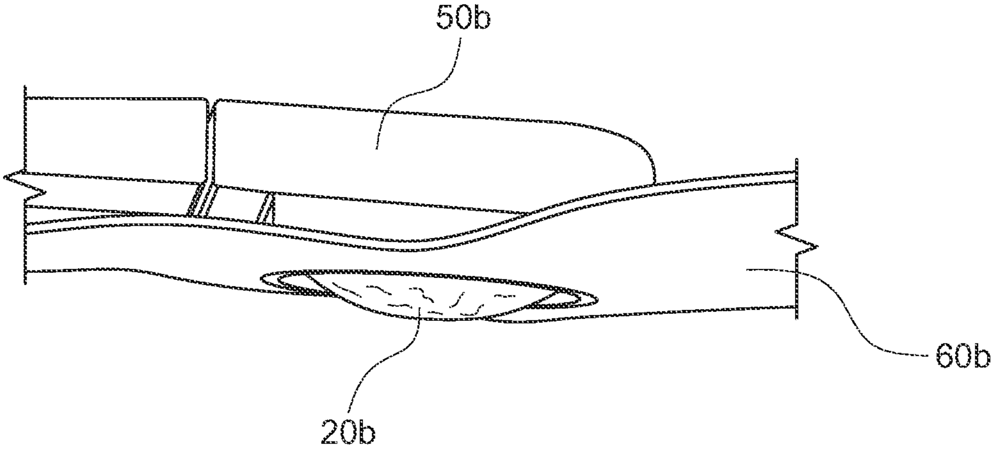
FIG. 13 is a side/bottom view of one embodiment of an ultrasound coupling device of the present invention, showing an ultrasound transducer coupled with the ultrasound coupling device of the present invention, illustrating the expandable foil embodiment of the bottom seal.

As shown in FIG. 13, when the ultrasound transducer is clipped into the ultrasound coupling patch, the ultrasound gel within the device moves in a forward direction with no gel escaping from the device and fully coating the ultrasound transducer surface.

Top and Bottom Seals with Contours to Allow for the First Aspect Described Herein of the Ultrasound Coupling Device, with Reduced Volumetric Area for Product Stacking and Shipping In a third aspect, since the invention described as the first aspect above increases the outward dimension of the ultrasound coupling patch along with introducing additional dead-space into the device, this reduces packing efficiency of putting one ultrasound coupling device on top of another device in a box. To increase packaging efficiency, the top seal of the ultrasound coupling device can be an inversion of the bottom seal. This is effective to displace the same volume from the top and bottom of the ultrasound coupling patch and allows for increased packing efficiency, as discussed below and illustrated in FIGS. 14-17.

In this aspect, there is provided an ultrasound coupling device that includes: (i) a gel component comprising a gel material effective to conduct acoustic energy; and (ii) a coupling compartment effective for holding the gel component in place. The coupling compartment includes: a wall-like structure having a sidewall, a top portion, and a bottom portion; a top seal removably integrated to the top portion of the wall-like structure; and a bottom seal removably integrated to the bottom portion of the wall-like structure. The top and bottom seals are formed to hold a known volume of gel in a defined location within the coupling compartment.

In one embodiment of this coupling device of the present invention, the top and bottom seals are made from aluminum foil.

In another embodiment, the top and/or bottom seal is made from a plastic part of the wall-like structure material.

In another embodiment, the top and bottom seals reduce non-gel volume within the device to less than 50%.

In another embodiment, this ultrasound coupling device further includes an adhesive fabric for interfacing the coupling device with a subject, where the adhesive fabric includes a vacant area in which the coupling compartment is situated for operation.

In another aspect, the present invention provides an ultrasound coupling system that includes: (i) the ultrasound coupling device disclosed herein above; and (ii) an ultrasound transducer configured for operable attachment to the ultrasound coupling device.

In another aspect, the present invention provides a method for performing physiotherapy on a subject. This method involves: (i) providing the ultrasound coupling system disclosed herein above; and (ii) using the system to apply therapeutic ultrasound energy to a subject, where the therapeutic ultrasound energy is generated by the transducer and emitted through the gel component of the coupling device.

In another aspect, the present invention provides a method for applying ultrasound energy to a subject. This method involves: (i) providing the ultrasound coupling system disclosed herein above; and (ii) using the system to apply ultrasound energy to a surface of a subject, where the ultrasound energy is generated by the transducer and emitted through the gel component of the coupling device. In one embodiment, applying the ultrasound energy to the surface of the subject is effective to alleviate pain in tissue of the subject in and around the surface.

FIGS. 14-17 illustrate various aspects of the above-described embodiment of the ultrasound coupling device of the present invention. With respect to FIGS. 14-17, the reference numbers of this embodiment of the ultrasound coupling device are identified in the paragraph below, as follows: As shown in FIGS. 14-17, ultrasound coupling device 10*c* includes: (i) gel component 20*c* comprising a gel material effective to conduct acoustic energy; and (ii) coupling compartment 30*c* effective for holding gel component 20*c* in place. Coupling compartment 30*c* includes: wall-like structure 32*c* having sidewall 33*c*, top portion 34*c*, and bottom portion 35*c*; top seal 40*c* removably integrated to top portion 34*c* of wall-like structure 32*c*; and bottom seal 42*c* removably integrated to bottom portion 35*c* of wall-like structure 32*c*. Top (40*c*) and bottom (42*c*) seals are formed to hold a known volume of gel in a defined location within coupling compartment 30*c*. Ultrasound coupling device 10*c* can further include adhesive fabric 60*c* for interfacing coupling device 10*c* with a subject, where adhesive fabric 60*c* includes a vacant area in which coupling compartment 30*c* is situated for operation.

Figure 14:
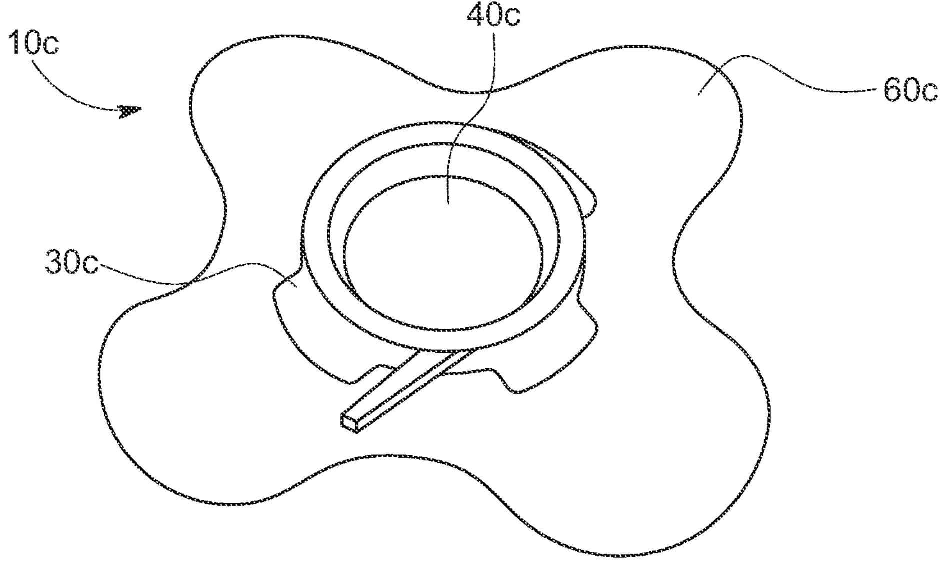
FIG. 14 is a top view of one embodiment of an ultrasound coupling device of the present invention, illustrating a formed top seal extending into a wall-like structure holding the coupling gel.

FIG. 14 illustrates the ultrasound coupling device with a formed top seal extending into wall-like structure holding coupling gel.

Figures 15, 16:
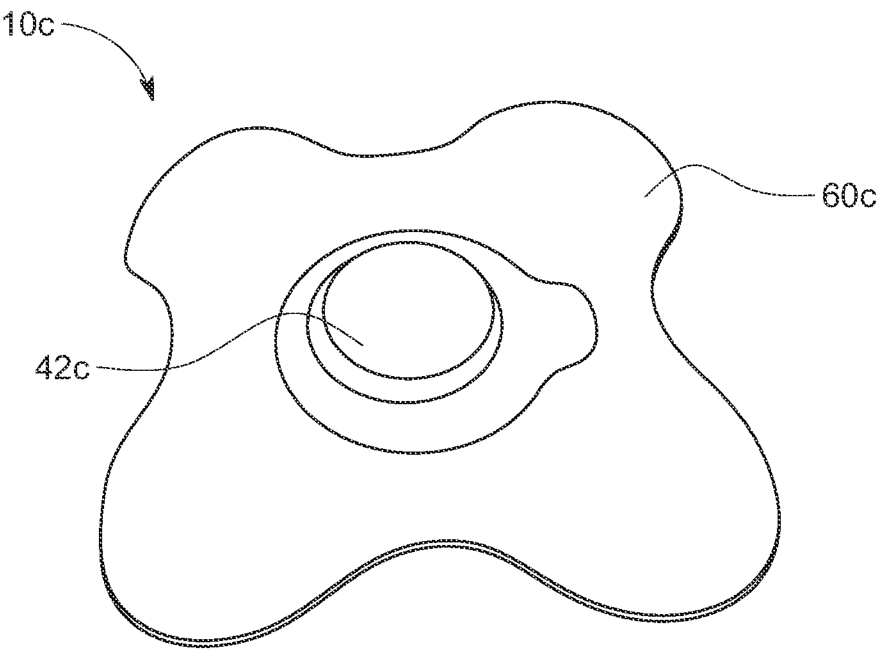
FIG. 15 is a bottom view of one embodiment of an ultrasound coupling device of the present invention.
FIG. 16 is a side view of four ultrasound coupling devices stacked on top of one another, each having adhesive fabric portions, with each ultrasound coupling device having preformed top and bottom seals of the gel containment structure.

FIG. 15 illustrates the bottom of the ultrasound coupling device, with formed seal extending outward from bottom of patch.

As shown in FIG. 16, formed seals of gel containment structure on both top and bottom of ultrasound coupling patch increase density packing of patches on top of one another as shown in the picture above.

Figure 17:
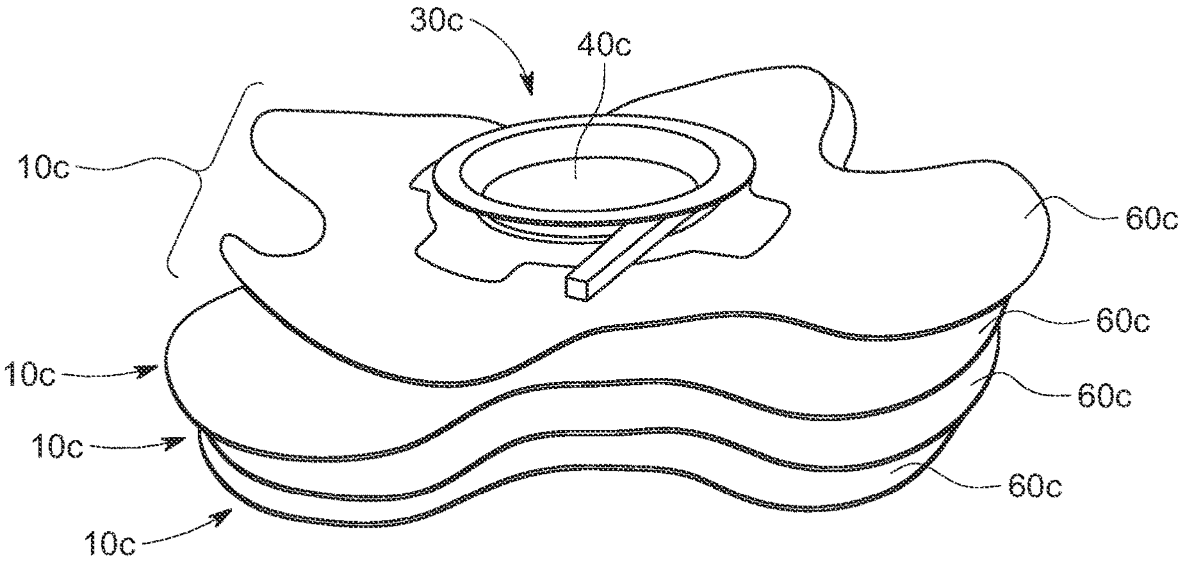
FIG. 17 is a top/side view of four ultrasound coupling devices stacked on top of one another, each having adhesive fabric portions, with each ultrasound coupling device having preformed top and bottom seals of the gel containment structure.

FIG. 17 illustrates another angle of four ultrasound coupling patches with gel-containment structures to maintain high density packing, and reduce void volume of non-gel within ultrasound coupling device.

The terms “a,” “an,” “the” and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references have been made to patents and printed publications throughout this specification. Citation of a reference herein shall not be construed as an admission that such reference is prior art to the present invention. All references cited herein are hereby incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Although the present invention has been described for the purpose of illustration, it is understood that such detail is solely for that purpose and variations can be made by those skilled in the art without departing from the spirit and scope of the invention which is defined by the following claims.

What is claimed is:

1. An ultrasound coupling device comprising:

a gel component comprising a gel material effective to conduct acoustic energy; and a coupling compartment effective for holding the gel component in place, wherein said coupling compartment comprises a wall structure having a sidewall, a top portion, and a bottom portion, a top seal removably integrated to the top portion of the wall structure, and a bottom seal removably integrated to the bottom portion of the wall structure, wherein said bottom seal is preformed to hold a desired volume of the gel material between an ultrasound transducer and the bottom seal and wherein the bottom seal is made of foil which is folded, partially folded, or crinkled, or the bottom seal is made of a flexible material in a flat form factor which is able to expand outward while allowing no gel material to escape from the bottom seal and the ultrasound coupling device when said ultrasound transducer is attached at the top portion of the wall structure, wherein said gel component is contained at least within a portion of a sidewall of the wall structure of the coupling compartment and at least a portion outside of the wall structure, and wherein said gel material is provided so as to have a thickness of between 0.25 mm and about 10 mm, a shape of the preformed seal to accommodate the ultrasound transducer, and to protrude beyond the bottom portion of the wall structure.

2. The coupling device according to claim 1, wherein the top and bottom seals are made from aluminum foil.

3. The coupling device according to claim 1, wherein the preformed bottom seal is integrated with an adhesive retainer liner of the coupling device.

4. The coupling device according to claim 1, wherein said gel material is selected from the group consisting of a gel, a gel composition, a hydrogel, and a low density cross-linked polymer hydrogel.

5. The coupling device according to claim 1 further comprising:

an adhesive fabric for interfacing the coupling device with a subject, wherein the adhesive fabric includes a vacant area in which the coupling compartment is situated for operation.

6. An ultrasound coupling system comprising:

an ultrasound coupling device according to claim 1; and an ultrasound transducer configured for operable attachment to the ultrasound coupling device.

7. A method for performing physiotherapy on a subject, said method comprising:

providing an ultrasound coupling system according to claim 6; and applying therapeutic ultrasound energy to a subject, wherein said therapeutic ultrasound energy is generated by the transducer and emitted through the gel component of the coupling device.

8. A method for applying ultrasound energy to a subject, said method comprising:

providing an ultrasound coupling system according to claim 7; and applying ultrasound energy to a surface of a subject, wherein said ultrasound energy is generated by the transducer and emitted through the gel component of the coupling device.

9. The method according to claim 8, wherein applying the ultrasound energy to the surface of the subject is effective to alleviate pain in tissue of the subject in and around the surface.

10. An ultrasound coupling device comprising:

a gel component comprising a gel material effective to conduct acoustic energy; and a coupling compartment effective for holding the gel component in place, wherein said coupling compartment comprises a wall structure having a sidewall, a top portion, and a bottom portion, a top seal removably integrated to the top portion of the wall structure, and a bottom seal removably integrated to the bottom portion of the wall structure, wherein a bottom seal is expandable to hold a desired volume of the gel material between an ultrasound transducer and the bottom seal and wherein the bottom seal is made of foil which is folded, partially folded, or crinkled, or the bottom seal is made of a flexible material in a flat form factor which is able to expand outward while allowing no gel material to escape from the bottom seal and the ultrasound coupling device when said ultrasound transducer is attached at the top portion of the wall structure, wherein said gel component is contained at least within a portion of a sidewall of the wall structure of the coupling compartment and at least a portion outside of the wall structure, and wherein said gel material is provided so as to have a thickness of between 0.25 mm and about 10 mm, a shape of the expandable bottom seal to accommodate the ultrasound transducer, and to protrude beyond the bottom portion of the wall structure when the ultrasound transducer is inserted.

11. The coupling device according to claim 10, wherein the expandable bottom seal is made from an elastic material which expands outward upon insertion of the ultrasound transducer.

12. The coupling device according to claim 10, wherein the expandable bottom seal is made from an aluminum foil seal which expands outward upon insertion of the ultrasound transducer.

13. The coupling device according to claim 10, wherein said gel material is selected from the group consisting of a gel, a gel composition, a hydrogel, and a low density cross-linked polymer hydrogel.

14. The coupling device according to claim 10 further comprising:

an adhesive fabric for interfacing the coupling device with a subject, wherein the adhesive fabric includes a vacant area in which the coupling compartment is situated for operation.

15. An ultrasound coupling system comprising:

an ultrasound coupling device according to claim 10; and an ultrasound transducer configured for operable attachment to the ultrasound coupling device.

16. A method for performing physiotherapy on a subject, said method comprising:

providing an ultrasound coupling system according to claim 15; and applying therapeutic ultrasound energy to a subject, wherein said therapeutic ultrasound energy is generated by the transducer and emitted through the gel component of the coupling device.

17. A method for applying ultrasound energy to a subject, said method comprising:
providing an ultrasound coupling system according to claim 15; and
applying ultrasound energy to a surface of a subject, wherein said ultrasound energy is generated by the transducer and emitted through the gel component of the coupling device.

18. The method according to claim 17, wherein applying the ultrasound energy to the surface of the subject is effective to alleviate pain in tissue of the subject in and around the surface.

19. An ultrasound coupling device comprising:
a gel component comprising a gel material effective to conduct acoustic energy; and
a coupling compartment effective for holding the gel component in place, wherein said coupling compartment comprises a wall structure having a sidewall, a top portion, and a bottom portion, a top seal removably integrated to the top portion of the wall structure, and a bottom seal removably integrated to the bottom portion of the wall structure,
wherein the top and bottom seals are formed to hold a known volume of gel in a defined location within the coupling compartment,
wherein a bottom seal is expandable to hold a desired volume of the gel material between an ultrasound transducer and the bottom seal and wherein the bottom seal is made of foil which is folded, partially folded, or crinkled, or the bottom seal is made of a flexible material in a flat form factor which is able to expand outward while allowing no gel material to escape from the bottom seal and the ultrasound coupling device when said ultrasound transducer is attached at the top portion of the wall structure, wherein said gel component is contained at least within a portion of a sidewall of the wall structure of the coupling compartment and at least a portion outside of the wall structure, and
wherein said gel material is provided so as to have a thickness of between 0.25 mm and about 10 mm, a shape of the bottom seal to accommodate an ultrasound transducer, and to protrude beyond the bottom portion of the wall structure.

20. An ultrasound coupling system comprising:
an ultrasound coupling device according to claim 19; and
an ultrasound transducer configured for operable attachment to the ultrasound coupling device.

21. A method for performing physiotherapy on a subject, said method comprising:
providing an ultrasound coupling system according to claim 20; and
applying therapeutic ultrasound energy to a subject, wherein said therapeutic ultrasound energy is generated by the transducer and emitted through the gel component of the coupling device.

22. A method for applying ultrasound energy to a subject, said method comprising:
providing an ultrasound coupling system according to claim 20; and
applying ultrasound energy to a surface of a subject, wherein said ultrasound energy is generated by the transducer and emitted through the gel component of the coupling device.

* * * * *